(12) United States Patent
Sidhu

(10) Patent No.: US 6,274,874 B1
(45) Date of Patent: Aug. 14, 2001

(54) PROCESS AND APPARATUS FOR MONITORING SURFACE LASER CLEANING

(75) Inventor: Jagjit Sidhu, Filton (GB)

(73) Assignee: BAE Systems plc, Farnborough (GB)

(*) Notice: Subject to any disclaimer, the term of this patent is extended or adjusted under 35 U.S.C. 154(b) by 0 days.

(21) Appl. No.: 09/412,394

(22) Filed: Oct. 5, 1999

Related U.S. Application Data

(63) Continuation of application No. PCT/GB98/03104, filed on Oct. 15, 1998.

(30) Foreign Application Priority Data

Oct. 24, 1997 (GB) .................................................. 9722406

(51) Int. Cl.$^7$ ................................................ G01N 21/64
(52) U.S. Cl. ................................ 250/461.1; 250/459.1
(58) Field of Search ................ 250/461.1, 459.1; 209/578

(56) References Cited

U.S. PATENT DOCUMENTS

| | | | |
|---|---|---|---|
| 4,641,650 | * 2/1987 | Mok | 128/303.1 |
| 5,256,880 | * 10/1993 | Loree et al. | 250/461.1 |
| 5,399,867 | 3/1995 | Kohno . | |
| 5,643,472 | * 7/1997 | Engelsberg et al. | 216/65 |
| 5,669,979 | 9/1997 | Elliott et al. . | |

FOREIGN PATENT DOCUMENTS

| | | |
|---|---|---|
| 4 216 189 | 11/1993 | (DE) . |
| 0 709 145 | 5/1996 | (EP) . |
| WO 88/08279 | 11/1988 | (WO) . |
| WO 95/07152 | 3/1995 | (WO) . |

OTHER PUBLICATIONS

Measures et al, "Analyzing Fluorescence Decay" Laser Focus, (Nov. 1974) p. 49.*

* cited by examiner

Primary Examiner—Georgia Epps
Assistant Examiner—Richard Hanig
(74) Attorney, Agent, or Firm—Nixon & Vanderhye P.C.

(57) ABSTRACT

A process and apparatus for monitoring the cleaning of a surface (1) by laser irradiation includes illuminating the surface (1) to be cleaned, being cleaned or having been cleaned by ultra-violet irradiation provided either by the cleaning laser or by a further source (5) sufficient to excite into fluorescence contaminants (10, 11) on the surface (1) which fluoresce under ultra-violet irradiation.

24 Claims, 2 Drawing Sheets

PROCESS AND APPARATUS FOR MONITORING SURFACE LASER CLEANING

This application is a continuation of PCT/GB98/03104, filed Oct. 15, 1998.

BACKGROUND OF THE INVENTION

1. Field of the Invention

This invention relates to a process and apparatus for monitoring the cleaning of a surface by laser irradiation.

2. Discussion of Prior Art

In many manufacturing processes such as for aircraft and automobiles components have to be cleaned prior to joining or coating. Conventionally this task is performed by wet cleaning using either water jets or solvents. In both cases the liquid residue remaining after cleaning has to be disposed of. Due to the impact of the solvents or the residue containing liquids upon the environment and the costs associated with the disposal of these chemicals, alternative cleaning techniques are desirable which do not involve the use and disposal of environmentally hazardous chemicals or residues.

It has been proposed to use a cleaning process which involves the irradiation of a surface by laser to remove contaminants such as solvents or epoxy particles. However it is also advisable to monitor the effectiveness of such laser cleaning processes and techniques have been proposed for doing this by plasma or ion emission analysis. One of the disadvantages of such monitoring techniques is that they can only monitor the very area the laser pulse is cleaning and no analysis can be performed on the area that is to be cleaned or the area that has been cleaned. Additionally the analysis process is time consuming and relatively expensive to carry out.

There is thus a need for a generally improved and simplified process of monitoring the cleaning of a surface by laser irradiation which can be used more effectively across the whole area of the surface to be cleaned.

SUMMARY OF THE INVENTION

According to one aspect of the present invention there is provided a process for monitoring the cleaning of a surface by laser irradiation in which the surface to be cleaned, being cleaned, or having been cleaned is illuminated by ultra-violet irradiation sufficient to excite into fluorescence contaminants on the surface which fluoresce under ultra-violet irradiation.

Preferably the intensity of fluorescence or the rate of decay of fluorescence is measured to indicate the area and thickness of contaminant on the surface.

Conveniently the intensity or rate of decay measured is utilised controllably to vary operating parameters of the cleaning laser.

Advantageously the ultra-violet irradiation is provided by an ultra-violet lamp.

Alternatively the ultra-violet irradiation is provided by an ultra-violet laser.

According to a further aspect of the present invention there is provided apparatus for cleaning a surface by laser irradiation, including a source of laser irradiation and means for irradiating the surface with ultra-violet radiation before, during or after cleaning, to monitor the area and extent of contaminant on the surface.

Preferably the apparatus includes a sensor for detecting the intensity or rate of decay and area of fluorescence excited on the surface by the ultra-violet irradiation.

Conveniently the apparatus includes means for controllably varying operating parameters of the cleaning laser in response to the detected intensity or rate of decay and area of fluorescence.

Advantageously the source of laser irradiation is an ultra-violet cleaning laser which additionally provides the means for irradiating the surface with the ultra-violet monitoring radiation.

Preferably the source of laser irradiation is a non ultra-violet or an ultra-violet cleaning laser and wherein the means for irradiating the surface with ultra-violet monitoring radiation is an ultra-violet lamp.

BRIEF DESCRIPTION OF THE DRAWINGS

For a better understanding of the present invention, and to show how the same may be carried into effect, reference will now be made, by way of example, to the accompanying drawings, in which.

DETAILED DISCUSSION OF PREFERRED EMBODIMENTS

Figure 1:
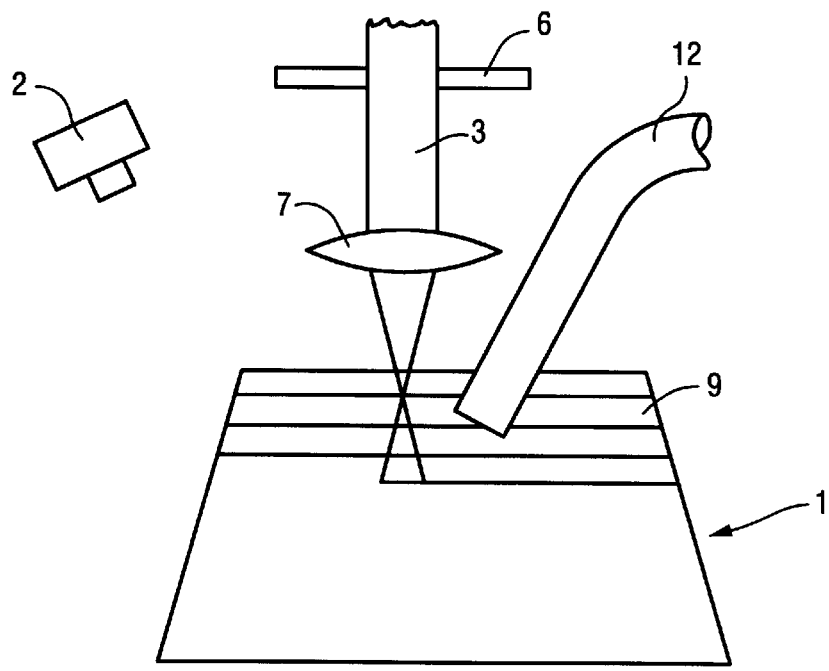
FIG. 1 is a perspective diagrammatic view of apparatus for cleaning and monitoring a surface according to a first embodiment of the present invention.

The apparatus and process according to the present invention for monitoring the cleaning of a surface by laser irradiation basically involves illuminating the surface 1, to be cleaned, being cleaned or having been cleaned by ultra-violet irradiation sufficient to excite into fluorescence contaminants on the surface 1 which fluoresce under ultra-violet irradiation. Many materials which form contaminants on a surface to be cleaned or cleaned fluorescence when irradiated with ultra-violet light. Examples of this are epoxy type contaminants. The intensity of fluorescence or the rate of decay of fluorescence is measured such as by means of an optical recording system such as a charge coupled device camera 2 to indicate the area and thickness of contaminant on the surface 1. In the embodiments of FIG. 1 the laser being used to clean the surface 1 is an ultra-violet source so that in this embodiment the ultra-violet irradiation 3 provides both the cleaning laser radiation and the monitoring ultra-violet irradiation. To this end the scatter from the cleaning laser irradiation beam 3 is used as the radiation required to cause fluorescence.

Figure 2:
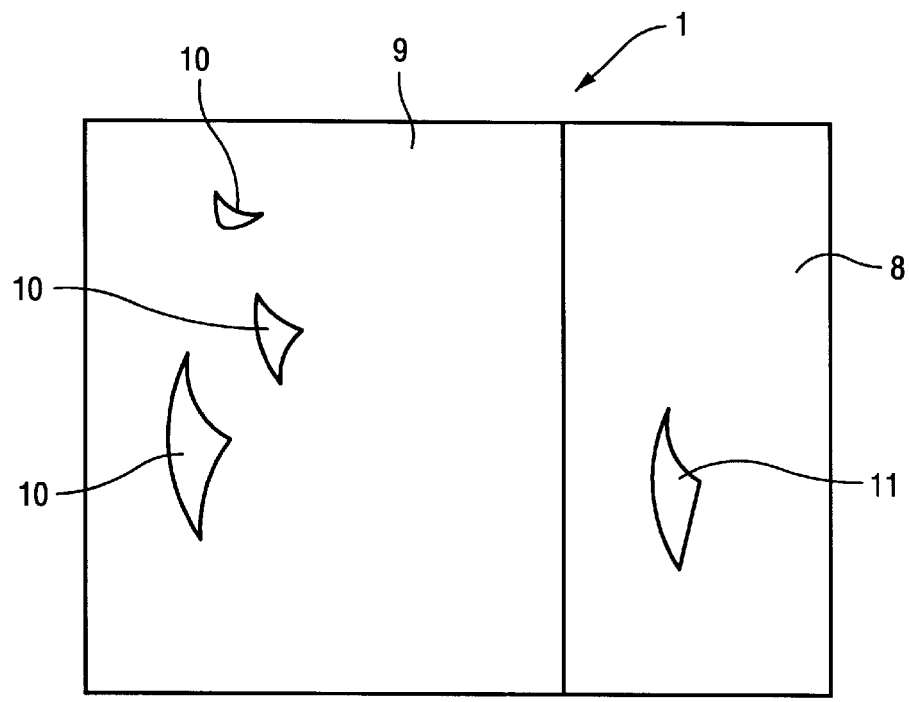
FIG. 2 is a diagrammatic view from above of a surface partially cleaned according to the apparatus of FIG. 1.
Figure 3:
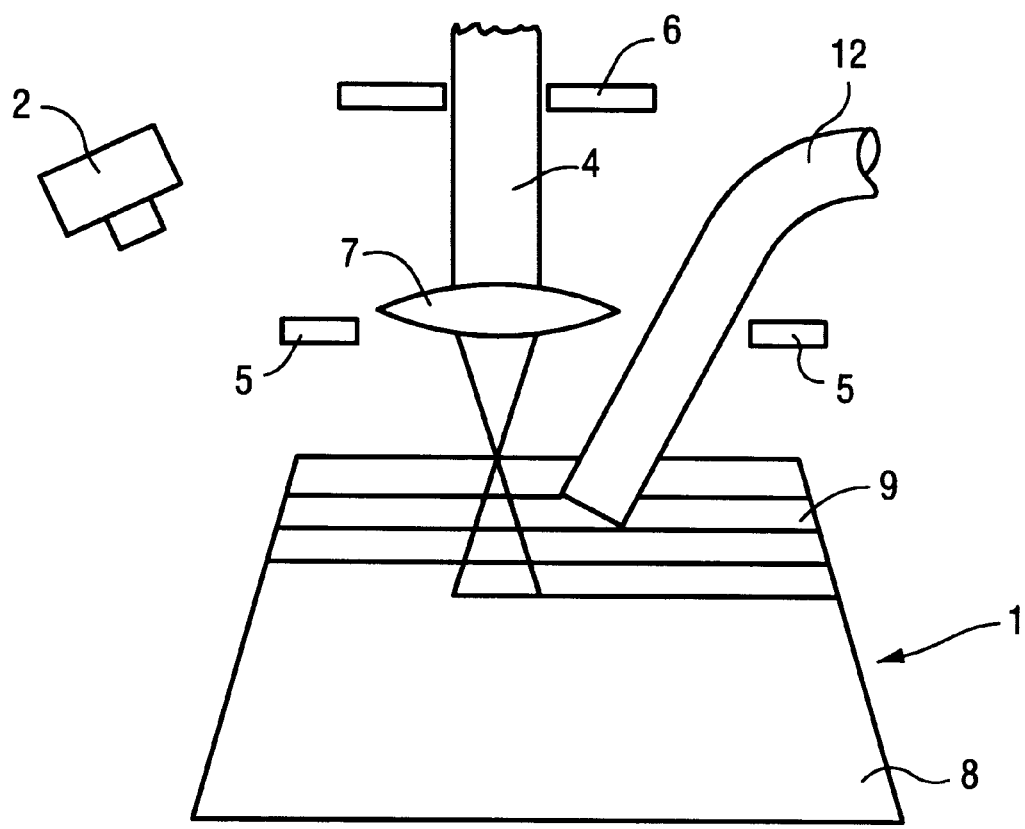
FIG. 3 is a perspective diagrammatic view of an apparatus for cleaning and monitoring the surface according to a second embodiment of the present invention.

Alternatively in the embodiment of FIG. 3, the cleaning laser providing a beam 4 of cleaning laser irradiation is a non ultra-violet source. In this case the required ultra-violet radiation can be supplied from any suitable source of ultra-violet irradiation such as one or more ultra-violet lamps 5. In the embodiments of FIGS. 1 and 2, the laser beam 3 or 4 is passed through an aperture plate 6 to provide a parallel beam of radiation and from thence through an imaging lens 7 onto the surface 1. The radiation is not focused as a spot on the surface 1 but rather as a line which is scanned across the surface 1 preferably by indexing the surface 1 with respect to the imaging lens 7.

Thus in FIGS. 1, 2 and 3 of the accompanying drawings an area to be cleaned is shown at 8. The cleaned area is shown at 9. As shown in FIG. 2 which is a plan view of the surface 1 from FIGS. 1 and 3, in the area already cleaned by laser irradiation there is not direct fluorescence except in regions 10 which represent residual uncleaned areas of contaminants which will fluoresce under the ultra-violet irradiation. In the area 8 to be cleaned there will be fluorescence from the whole surface when irradiated with ultra-violet irradiation with a region of greater thickness contaminant 11 showing up with a different intensity of fluorescence or rate of decay or fluorescence from the remaining uncleaned area 8.

Thus in the embodiments of FIGS. 1 and 3 when laser cleaning takes place, removed contaminant material and fumes is extracted via an extraction pipe 12. The fluorescence monitoring can be effected in different ways. For example as the laser 3 or 4 is cleaning an area 9 of the surface 1, the fluorescence reveals areas that have been cleaned successfully, areas that the laser has not cleaned successfully such as the areas 10 and areas 8 and 11 that the laser is yet to clean. Using the optical recording system such as the camera 2 which acts as a sensor for detecting the intensity or rate of decay of the fluorescence, the areas of residual contaminants on the cleaned surface area 9 can be recorded, such as in FIG. 2 and used to assess the areas that the laser needs to return and clean. Alternatively fluorescence can be used to estimate the thickness of the contaminant such as in the area 11, the head of the area already cleaned such as in the area 8 to be cleaned, and the laser parameters can be adjusted such as by varying the laser powers or scan speed, to account for the different contaminant thickness and position.

Frequently areas of greater thickness of contaminant such as the area 11 on FIG. 2 has different fluorescence characteristics. This may be a different intensity of fluorescence or a different fluorescence decay time. This information is used to estimate the thickness of the film of contaminant at area 11 so that the cleaning laser parameters may be adjusted prior to cleaning of the area 11 to be optimum for the thickness of the contaminant film in this area. For example if the contaminant area 11 is greater in thickness than the surrounding area 8 then the laser irradiation exposure time can be increased in the area 11 only rather than over the whole of the area 8.

It is to be understood that the ultra-violet lamps 5 may be employed for monitoring in the absence of an ultra-violet source cleaning laser but can also be used in addition to an ultra-violet source cleaning laser to augment the ultra-violet radiation from the latter source.

What is claimed is:

1. A method of monitoring the cleaning of contaminats that fluoresce from a surface of a man made component by irradiation from a cleaning laser, said method comprising the steps of:

illuminating said surface with radiation causing said contamination to fluoresce;

measuring a characteristic of said fluorescence; and adjusting said cleaning laser, responsive to said measuring step, to remove said contamination.

2. The method according to claim 1, wherein in said measuring step, said characteristic is intensity of said fluorescence.

3. The method according to claim 1, wherein in said measuring step, said characteristic is rate of decay of said fluorescence.

4. The method according to claim 1, wherein in said illuminating step, said radiation is ultra-violet radiation.

5. The method according to claim 1, wherein said adjusting step comprises scanning said cleaning laser over said surface.

6. The method according to claim 5, wherein said scanning step includes varying speed of said scan over said surface.

7. The method according to claim 5, wherein said scanning step includes increasing said intensity of radiation from said cleaning laser to remove any said contamination.

8. The method according to claim 5, wherein said scanning step includes repeatedly scanning said cleaning laser over any said contamination until said contamination has been removed.

9. The method according to claim 4, wherein said ultra-violet radiation is provided by an ultra-violet lamp.

10. The method according to claim 4, wherein said ultra-violet radiation is provided by an ultra-violet laser.

11. The method according to claim 4, wherein said cleaning laser is provided by an ultra-violet laser.

12. The method according to claim 4, wherein said measuring step comprises viewing said surface with an optical recording system.

13. An apparatus for monitoring the cleaning of contamination that fluoresces from a surface of a man made component by irradiation from a cleaning laser, said apparatus comprising:

a source of radiation for illuminating said surface and causing said contamination to fluoresce;

a sensor for measuring a characteristic of said fluorescence; and means for adjusting said cleaning laser, responsive to said sensor, to remove said contamination.

14. The apparatus according to claim 13, wherein in said sensor, said characteristic is intensity of said fluorescence.

15. The apparatus according to claim 13, wherein in said sensor, said characteristic is rate of decay of said fluorescence.

16. The apparatus according to claim 13, wherein in said source of radiation, said radiation is ultra-violet radiation.

17. The apparatus according to claim 13, wherein said means for adjusting comprises a scanner for scanning said cleaning laser over said surface.

18. The apparatus according to claim 17, wherein said means for adjusting comprises varying the scanning speed of said scanner.

19. The apparatus according to claim 17, wherein said means for adjusting includes increasing said intensity of radiation from said cleaning laser to remove any said contamination.

20. The apparatus according to claim 17, wherein said means for adjusting includes means for repeatedly scanning said cleaning laser over any said contamination until said contamination has been removed.

21. The apparatus according to claim 16, wherein said ultra-violet radiation is provided by an ultra-violet lamp.

22. The apparatus according to claim 16, wherein said ultra-violet radiation is provided by an ultra-violet laser.

23. The apparatus according to claim 16, wherein said cleaning laser is provided by an ultra-violet laser.

24. The apparatus according to claim 16, wherein said sensor comprises an optical recording system.

* * * * *